United States Patent [19]

Albers

[11] Patent Number: 5,556,524
[45] Date of Patent: Sep. 17, 1996

[54] ELECTRON-CONDUCTING MOLECULAR PREPARATIONS

[75] Inventor: Martin Albers, Tampere, Finland

[73] Assignee: Valtion Teknillinen Tutkimuskeskus, Finland

[21] Appl. No.: 389,597

[22] Filed: Feb. 16, 1995

[30] Foreign Application Priority Data

Feb. 16, 1994 [FI] Finland .................................. 940738

[51] Int. Cl.$^6$ ............................ C25B 13/00; H01B 1/00; G01N 27/26
[52] U.S. Cl. ...................... 204/296; 204/400; 204/403; 204/415; 252/500; 429/192; 429/198; 429/213; 429/249
[58] Field of Search ........................... 252/500; 429/192, 429/198, 213, 249; 204/415, 296, 403

[56] References Cited

U.S. PATENT DOCUMENTS 5,320,725  6/1994  Gregg et al. .......................... 204/403

FOREIGN PATENT DOCUMENTS

0314009A3  11/1990  European Pat. Off. .
05070455    9/1991  Japan .

OTHER PUBLICATIONS

Albers et al, Preparation of extended di (4–pyridyl) thiophene oligomers, 1995, Tetrahedron, 51(13) 3895–904.
Takahashi, K. J. Chem. Soc. Chem. Commun. (8), 620–2 (1992).
Nakajima, R et al. Bull. Chem. Soc. Jpn, 63(2), 636–7 (1990).
Takahashi, et al., One–Pot Synthesis and Redox Properties of Conjugation–Extended 4,4'–Bipyridines and Related Compounds. New Ligands Consisting of a Heterocyclic Three–Ring Assembly, The Chemical Society of Japan, Bull. Chem. Soc., vol. 65 (1992) pp. 1855–1859 no month available.
Nakajima, et al., Synthesis and Spectral Properties of 5,5'–Di(4–pyridyl)–2,2'–bithienyl as a New Fluorescent Compound, The Chemical Society of Japan, Bull. Chem. Soc., vol. 63, No. 2, (1990), pp. 636–637 no month available.
Sariciftci, et al., In Situ Spectroscopic Studies on Viologen Functionalized Poly(3–Alkylthiophenes) During Electrochemical Redox Processes, Springer Series in Solid–State Sciences, vol. 102 (1992), pp. 176–179 no month available.
Chemical Abstracts, vol. 118 (1993), p. 8, Item 118:22756h, Sariciftci, et al., In-situ spectroscopic studies on viologen functionalized poly(3–alkylthiophenes) during electrochemical redox processes. no month available.
Chemical Abstracts, vol. 115 (1991), p. 614, Item 115:192253x, Hillman, et al., Electroactive bilayers employing conducting polymers. Part III. Kinetic v.s. diffusional control of outer layer switching rate. no month available.
Chemical Abstracts, vol. 115 (1991), p. 614, Item 115:192256a, Hillman, et al., Electroactive bilayers employing conducting polymers. 2. Speciation by in situ spectroscopy. no month available.

*Primary Examiner*—Bruce F. Bell
*Attorney, Agent, or Firm*—Pollock, Vande Sande & Priddy

[57] ABSTRACT

The invention relates to an electron-conducting molecular preparation designed to act as a conductor by receiving an electron at its one end and conducting the electron along its molecular structure to its other end. The molecule in the preparation has the following general formula (I):

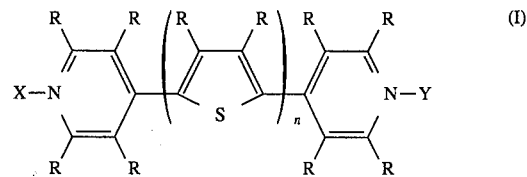

wherein n represents an integer from 1 to 12 the groups X and Y are identical or different and denote functional substituents bound to the pyridine nitrogen, or one or both of X and Y are absent, and

R, being identical or different, represent a hydrogen atom or an aliphatic side chain introduced for enhancing the solubility of the molecule in organic solvents, for example a branched or unbranched alkyl or alkoxy group containing any number of carbon atoms.

The molecular preparations can be incorporated in a substantially insulating membrane to act as conductors between an electroactive species and an electrode in diagnostic determinations.

20 Claims, 9 Drawing Sheets

ELECTRON-CONDUCTING MOLECULAR PREPARATIONS

BACKGROUND OF THE INVENTION

Controlled enhancement of electronic conductivity in highly isolating thin molecular membranes by new types of intrinsically conductive organic or organometallic compounds is highly in demand, because this gives possibilities for improving the sensitivity and selectivity of electrochemical processes occurring at the solid/liquid interface [Atta N. F. et al. (1991) Biosensors and Bioelectronics 6, 333–341; Hable C. T. & Wrighton M. S. (1993) Langmuir 9, 3284–3290].

Generally, for application in chemical sensing devices, conductivity is desired through thin molecular membranes of different types, including biological membranes, biomimetic membranes and thin polymer films, with a thickness varying between 50 and 100 Å, [Merz A. (1990) Top. Curr. Chem. 152, 51–90; Ottova-Leitmannova A. & Tien H. T. (1992) Prog. Surf. Sci. 41/4, 337–445]. Additionally, the introduction of electronic conductivity in highly isolating bulk polymers is actively studied, particularly for electronic shielding purposes [Cao Y. et al. (1993) Synth. Met. 55–57, 3514–3519].

Figure 1A:
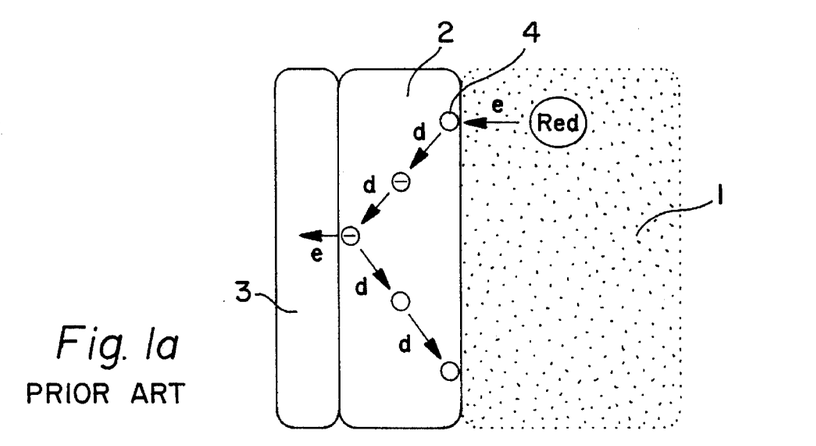
FIGS. 1a–c illustrate three well-known mechanisms of electron-transport in organic membranes.
Figure 1B:
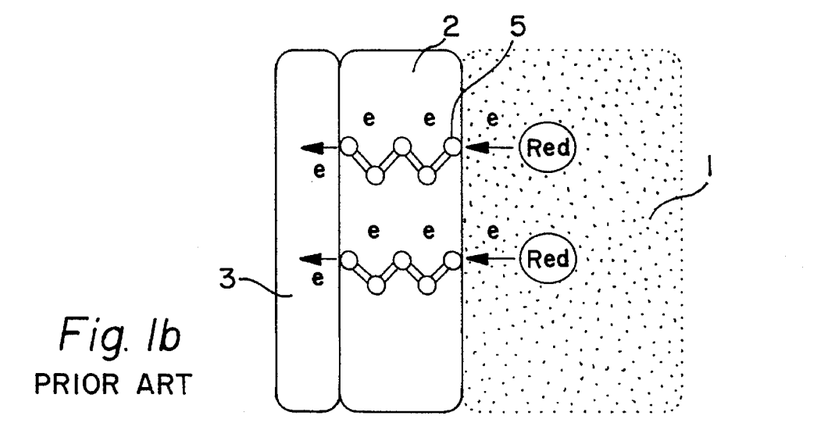
Figure 1C:
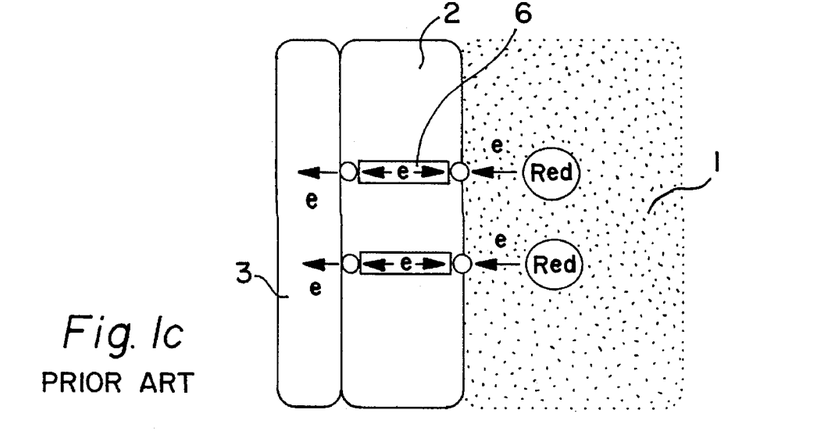

Transport of electrons may be induced by, in principle, three types of mechanisms, as illustrated in FIGS. 1a–c, where an electrolyte solution is denoted by 1, an insulating membrane by 2, a metallic electrode by 3, electron transfer by arrow e, and an electron donor (reductor) by "Red".

In the first mechanism, of FIG. 1a, electron transfer rates are largely controlled by the diffusion of the electroactive species through the membrane, which is a slow process. With multiple redox centres the process of conduction, as depicted in FIG. 1b, is controlled by the self-exchange rate of the redox species, the mean distance between the redox species and the dielectric constant of the membrane phase. This is generally a much faster conduction mechanism than that of mediated electron transfer.

In the last case, with an extended $\pi$-electron system, as illustrated in FIG. 1c, electrons are delocalised over the whole length of the molecule, a conduction process that is about 5 orders of magnitude faster than that of conduction through redox chains. Electron transfer with these types of molecules is in principle the most effective. With membrane thicknesses below 40 Å an additional conduction mechanism may occur, namely that of electron tunnelling [Thompson D. H. P. & Hurst J. K. (1988) in: Carter F. L. et al. (Ed.) 'Molecular Electronic devices' Elsevier, Amsterdam, 1988. pp. 413–425].

In earlier studies by other workers it has been shown that carotenes, modified with terminal pyridinium groups, "caroviologens" (structures according to formula II), may be incorporated in liposome bilayer lipid membranes in a characteristic through-membrane orientation, which is a main prerequisite for effective electron transfer through the membrane [Arrhenius T. S. et al. (1986) Proc. Natl. Acad. Sci. 83, 5355–5359; Johansson L. B.-Å et al. (1989) J. Phys. Chem. 93, 6751–6754.].

FIG. 1a shows schematically the transport by electron-mediation, in which a hydrophobic electroactive species 4, the "mediator", receives one or more electrons at one side of the isolating membrane 2, subsequently diffuses (arrow d) to the opposite side of the membrane and donates the electron(s) to the electrode. The oxidised mediator is denoted by a black dot and the reduced mediator by a minus sign. Examples, known in the art, are the incorporation of certain small dye molecules or highly conjugated organic molecules into bilayer lipid membranes [Janas T. et al. (1988) Bioelectrochem. & Bioenerg. 19, 405–412; Kutnik Y. et al. (1986) Bioelectrochem. & Bioenerg. 16, 435–447].

FIG. 1b shows schematically the transport by electron exchange ('hopping'), using a molecule that contains multiple electroactive species (a chain 5 of redox centres), fixed at predetermined distances from each other by a chemical tether. In this system electrons are received at one side of the membrane and jump between the electroactive centres across the membrane.

FIG. 1c shows schematically the transport by electron-delocalisation, using a molecule 6 containing an extended $\pi$-electron system, capable of receiving electrons at one side of the membrane 2 and delocalising the electron nearly instantaneously to the other side of the membrane by a quantum-chemical mechanism. Such molecules are acting as a direct electronic wire between an electroactive species and the electrode surface.

Although the caroviologens are functionally active as molecular conductors, the conductivity change, observed in liposomes, was not very large: only a 4 times increase of electronic conductivity was observed for an alkyl sulfonated caroviologen derivative [Lehn J.-M. (1991) in: Schneider H.-H. & Dürr H. (Ed.), 'Frontiers in Supramolecular Organic Chemistry and Photochemistry' VCH Publ, Weinheim, 1991. pp. 1–28]. Further research on more optimal conductors has mainly been concerned with further modification of the terminal groups of the polyene chain [Blanchard-Desce M. et al. (1988) J. Chem. Soc., Chem. Commun., 737–739; Thomas J. A. et al. (1992) J. Chem. Soc., Chem. Commun., 1796–1798; Bubeck C. et al. (1992) Adv. Mater. 4, 413–416].

It is known, however, that the chemical stability of the polyenes, and particularly the carotenes, is not very high. Also polyene structures exhibit photochemical cis-trans-isomerization, which affects the planar conformation of the molecule and the incorporation in thin organic films [Carter F. L. et al. in: Carter F. L. et al. (Ed.) 'Molecular Electronic devices' Elsevier, Amsterdam, 1988. pp. 465–481]. Particularly the coplanarity of the whole $\pi$-electron system, is an important condition for efficient conduction.

SUMMARY OF THE INVENTION

The object of the present invention is to provide a new class of conductors, which omits much of the problems encountered with the polyene-linked and carotene-linked di-pyridyls and which has excellent intrinsic conductivity in thin organic molecular films.

In the present invention new types organic compounds are disclosed, which show a high degree of intra-molecular electronic conductivity. The compounds according to the invention are characterized by an oligomeric thiophone structure terminated at both ends by a pyridine functional group. The new class of compounds, "thienoviologens" (formula I), are capable of efficient electron transfer through highly isolating thin organic films and may be used for the construction of functional molecular assemblies. The compounds according to the invention may be applied in various electronic devices, such as molecular electronics components, chemical sensors and biosensors or in various electrochemical processes relying on efficient electron transfer at electrode surfaces.

DETAILED DESCRIPTION OF THE INVENTION

In the present invention a novel class of compounds, acting as effective electronic conductors in thin organic films, with the general structure (I) are disclosed. These compounds according to the present invention are referred to as "Thienoviologens". In structure (I), n denotes an integer number ranging from 1 to 12 and X and Y represent functional entities attached to the pyridine nitrogens, which may be different or the same in structure. One or both of the entities X or Y may also be absent. Additionally, the carbon atoms of the thiophene and pyridine rings may be substituted with hydrogen or with branched or unbranched aliphatic alkyl chains or branched or unbranched alkoxy chains (R) of arbitrary length, solely for the enhancement of solubility of the compounds in organic solvents or for introducing the possibility for production of polymer blends, as is known for the man skilled in the art in respect of similar oligomers and polymers [ten Hoeve W. et al. (1991) J. Am. Chem. Soc. 113, 5887–5889; Laakso J. et al. (1990) Synth. Met. 37, 145–150.; Callender C. L. et al. (1991) Thin Solid Films 204, 451–457]. The above-mentioned side groups do not participate in the electron transfer, and the main emphasis of the present invention is in the structure of the conducting chain of the molecule.

The structure of the pyridine end groups can vary according to the application. For example, pyridine, itself not redox-active, can act as a ligand for metal complex formation, since some of the complexes are already known as models for studying intramolecular charge transfer [Launey J. P. et al. in: Carter F. L. et al. (Ed.) "Molecular Electronic Devices", Elsevier, Amsterdam, 1988]. The compounds of the invention can be placed as electronic conductors in a membrane that is substantially isolating (FIG. 1c). The membrane can be a molecular monolayer, bilayer or multilayer, such as a Langmuir-Blodgett film. The amphiphilic character of the molecules and their solubility in organic solvents can be enhanced by introducing longer alkyl chains at the pyridine nitrogens and carbon backbone of the molecule. These substitutions do not greatly interfere with the intrinsic conductivity of the molecules, similarly as with the oligothiophenes.

The alkyl chains attached to the pyridine nitrogen may also include other functionalities at the opposite end of the alkyl chain, such as a sulfonate group for formation of a zwitterionic compound suitable for incorporation in natural bilayer lipid membranes, or a thiol group for direct linking of the molecule to a gold electrode.

The insulating membrane together with the thienoviologen molecules may be attached directly to an electrode surface by known methods. The external redox species to be analysed (FIG. 1c, "Red") can be a small electro-active compound, but also a large compound, such as a redox-biomolecule, involved in biological electron-transfer. These compounds can be attached to the other end of the thienoviologen, in which case the thienoviologen acts according to the invention as a direct electronic wire between the external redox species and the electrode. The linkage can be effected through the pyridine end group by a strong non-covalent interaction, such as a hydrogen-bridge, an electrostatic interaction or a charge transfer interaction. The linkage may also be effected by a complex-formation reaction between the pyridine nitrogen and a suitable metal ion, such as zinc, copper, iron, ruthenium or osmium ions. Finally, the attachment may be of a covalent nature by electrophilic substitution of the pyridine nitrogen.

As specific examples of our invention, two representative compounds with n=2 and n=3 are introduced of which the induction of electronic conductivity is demonstrated in thin organic molecular films. Compounds of formula (I) having several thiophene units, i.e. with n between 2 and 12 are preferred, and compounds where n is from 3 to 12 are particularly preferred because of their molecular lengths, which is an important factor for bridging desired distances.

The first compound is an oligomeric thiophene with two thiophene units terminated by a pyridine functional group at one side and a pyridinium functional group on the opposite side, 5-[4-(N-methyl)pyridinium]-5'-(4-pyridyl)-2,2'-bithiophene iodide, structure (III), "MeIPT2P". Compounds of this type are bifunctional, having a free pyridine functional group able to form a complex with a metal electrode, such as gold, platinum or silver, or with a metal ion, such as copper.

(III)

(IV)

zinc complex. Non-alkylated bipyridylthiophene oligomers can be prepared with up to 5 units between the pyridine groups (PT$_5$P) with this method. Longer thienoviologens cannot be readily formed with the same method because dibromo-substituted thiophene oligomers with more than three thiophene units are too badly soluble in the reaction medium, THF, and have thus too low reactivity towards the pyridylthiophene organozinc reagent. In this case, however, partial substitution of the thiophenes with aliphatic alkyl side chains may be used, as discussed earlier, to improve the solubility of the reactants and final products in the organic solvent.

The second compound is an oligomeric thiophene consisting of three oligomeric thiophenes terminated by two pyridinium groups, 5,5"-bis[4-(N-methyl)pyridinium]-2, 2':5',2"-terthiophene di-iodide, structure (IV).

Figure 2A:
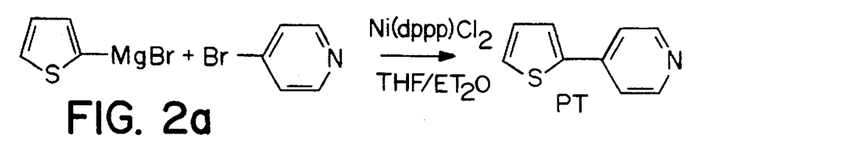
FIG. 2a–e show the synthesis schemes followed for producing the compounds according to the present invention.
Figure 2B:
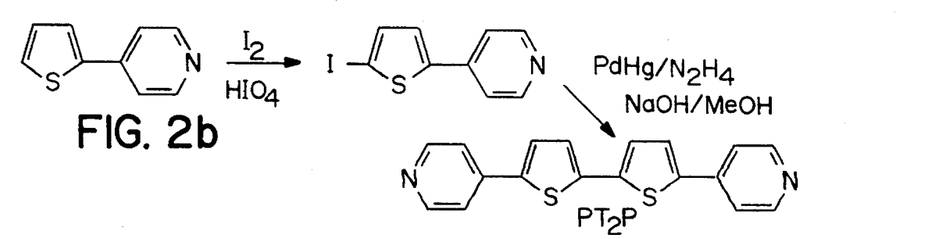
Figure 2C:
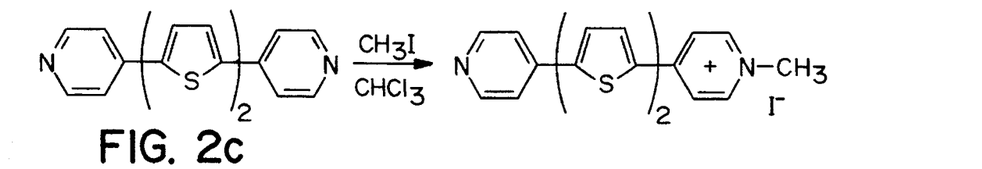
Figure 2D:
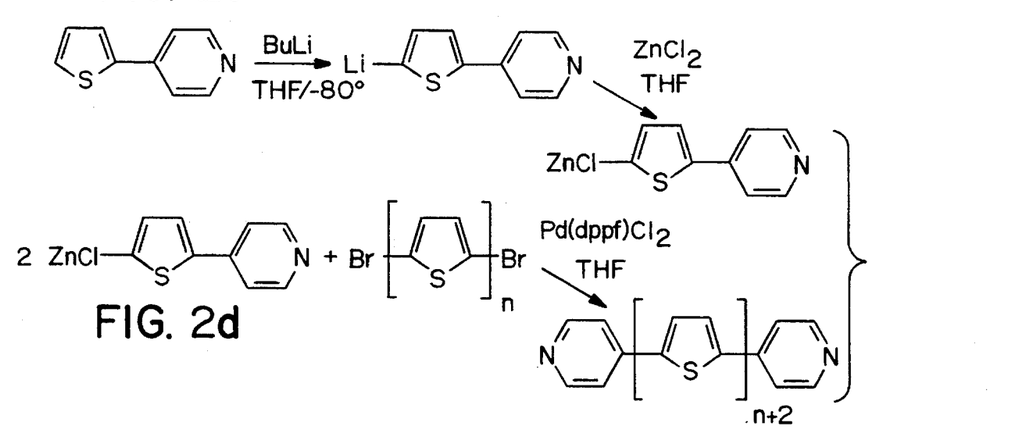
Figure 2E:
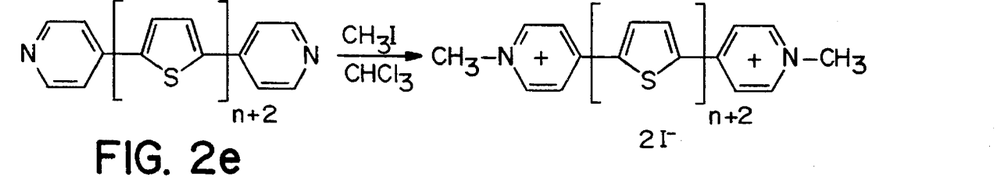

Finally, methylation of the bipyridylthiophene oligomers to the thienoviologens can be readily achieved by reaction with methyliodide in dilute chloroform solution (FIG. 2e). Products generally form very slowly during one week and precipitate as orange-red to dark-red needles. PT$_2$P yielded the mono-methylated compound (III), MeIPT$_2$P, while longer oligomers PT$_3$P and PT$_4$P yielded the dimethylated products resp. (MeI)$_2$PT$_3$P (IV) and (MeI)$_2$PT$_4$P. PT$_5$P is already a very insoluble compound, but was prepared in reasonably high yields via the scheme of FIG. 2d with n=3. The synthesized molecules were characterised by elemental analysis, $^1$H-NMR, IR, UV/VIS and mass spectrometry. UV/VIS spectra showed absorption maxima (in DMSO) at 385 nm for PT$_2$P and 418 nm for PT$_3$P. On acidification these maxima shifted to 427 nm and 463 nm respectively. The $^1$H-NMR data of relevant pyridyl thiophene oligomers and some of their intermediates is given in the following Table 1.

Synthetic Route

The synthesis schemes followed for producing extended di-(4-pyridyl)thiophenes and subsequently the thienoviologens of the present invention are given in FIG. 2. Although the shortest intermediates 5,5'-di(4-pyridyl)-2,2'-bithiophene, "PT$_2$P" and 2,5-di(4-pyridyl)-thiophene, "PTP" have been prepared earlier [Nakajima R. et al. (1990) Bull. Chem. Soc. Jpn. 63, 636–637; Takahashi K. & Nihira T. (1992) Bull. Chem. Soc. Jpn. 65, 1855–1859.], no explicit synthesis methods have been described for the longer oligomers (n>2). Good yields of these longer oligomers with n between 3 and 12 were obtained via a synthesis route using an organozinc intermediate, and [1,1'-bis-(diphenylphosphino)-ferrocene]-palladium(II) chloride, Pd(dppf)Cl$_2$, as a crosscoupling catalyst (FIG. 2d). These methods are known in the art for producing similar compounds [Tamao K. et al. (1982) Tetrahedron 38, 3347–3354; Carpita et al. (1985) Tetrahedron 41, 1919–1929.]. The product precipitated as a

TABLE 1

$^1$H-NMR data of pyridyl thiophene oligomers.

| | | Chemical shift δ/ppm | | | | | | | | | |
|---|---|---|---|---|---|---|---|---|---|---|---|
| Compound | Solvent | a | b | β$_1$ | β$_2$ | β$_3$ | β$_4$ | β$_5$ | β$_6$ | β$_7$ | β$_8$ |
| PT$_2$ | CDCl$_3$ | 8.59 | 7.46 | 7.43 | 7.19 | 7.25 | 7.05 | 7.28)* | | | |
| | | | | 7.44)$^c$ | 7.23)$^c$ | | | | | | |
| | DMSO-d$_6$ | 8.56 | 7.64 | 7.79 | 7.40 | 7.42 | 7.13 | 7.58)* | | | |
| PT—Br | CDCl$_3$ | 8.59 | 7.38 | 7.10 | 7.26 | | | | | | |
| | | | | 7.10)$^c$ | 7.30)$^c$ | | | | | | |

TABLE 1-continued $^1$H-NMR data of pyridyl thiophene oligomers.

[Structure 1: pyridyl-(thiophene)$_4$-Br oligomer with positions labeled a, b, β$_1$, β$_2$, β$_3$, β$_4$, β$_5$, β$_6$, β$_7$, β$_8$]

[Structure 2: (H$_3$C→N)(+)-pyridyl-(thiophene)$_5$-pyridyl-N(←CH$_3$)(+) oligomer with positions labeled a, b, β$_1$, β$_2$, β$_3$, β$_4$, β$_5$]

| Compound | Solvent | Chemical shift δ/ppm | | | | | | | | | |
|---|---|---|---|---|---|---|---|---|---|---|---|
| | | a | b | β$_1$ | β$_2$ | β$_3$ | β$_4$ | β$_5$ | β$_6$ | β$_7$ | β$_8$ |
| PT$_2$—Br | CDCl$_3$ | 8.60 | 7.44 | 7.41 | 7.12 | 7.01)$^x$ 7.03)$^c$ | 6.98)$^x$ 7.01)$^c$ | | | | |
| PT$_3$—Br | CDCl$_3$ | 8.60 | 7.46 | 7.44 | 7.19 | 7.14 | 7.05 | 6.99)$^x$ | 6.94)$^x$ | | |
| PT$_4$—Br | CDCl$_3$ | 8.60 | 7.47 | 7.44 | 7.20 | 7.16 | 7.11 | 7.09 | 7.05 | 6.99)$^x$ | 6.94)$^x$ |
| PTP | CDCl$_3$ | 8.64 | 7.51 | 7.54 7.57)$^c$ | | | | | | | |
| PT$_2$P | CDCl$_3$ | 8.61 | 7.47 | 7.46 7.48)$^c$ | 7.26 7.30)$^c$ | | | | | | |
| | DMSO-d$_6$ | 8.59 | 7.67 | 7.85 | 7.54 | | | | | | |
| methylated | DMSO-d$_6$ | 8.86 | 8.32 | 8.26 | 7.72 | 7.68 | 7.90 | 7.68)$^b$ | 8.61)$^a$ | | |
| PT$_3$P | CDCl$_3$ | 8.60 | 7.47 | 7.46 | 7.22 | 7.19 7.21)$^c$ | | | | | |
| | DMSO-d$_6$ | 8.57 | 7.64 | 7.80 | 7.41 | 7.26 | | | | | |
| methylated | DMSO-d$_6$ | 8.87 | 8.33 | 8.27 | 7.73 | 7.66 | | | | | |
| PT$_4$P | CDCl$_3$ | 8.60 | 7.47 | 7.43 | 7.19 | 7.15 | 7.11 | | | | |
| methylated | DMSO-d$_6$ | 8.85 | 8.31 | 8.26 | 7.69 | 7.61 | 7.52 | | | | |
| PT$_5$P | CDCl$_3$ | 8.60 | 7.47 | 7.44 | 7.20 | 7.16 | 7.11 | 7.11 | | | |

)*chemical shift of the thiophene a-proton
)$^c$calculated value
)$^a$a-proton of unmethylated pyridine ring
)$^b$b-proton of unmethylated pyridine ring
)$^x$assignment uncertain

Electrode Coating

The process of self-assembly is defined as the spontaneous organised irreversible adsorption of molecules on a solid surface. Here, particularly the self-assembly of alkylmercaptans on gold surfaces has been used, a process which offers a convenient system for assessing the conductivity of different compounds [Bain C. D. (1989) J. Am. Chem. Soc. 111, 321–335.; Stelzle M. (1993) J. Physics Chem. 97, 2974–2981].

Planar thin film gold electrodes (of 9 mm$^2$) were coated with a single molecular layer of octadecyl-mercaptan (hereafter referred to as ODM) as follows: The electrodes are cleaned by an KF argon plasma for 0.5 min at 0.8 kV and a pressure of 10 mTorr, and transferred to a coating solution containing 1 mM ODM in ethanol. The electrodes were left in the solution for 18 hours and then thoroughly rinsed with ethanol.

Conductivity Measurements

Figure 3:
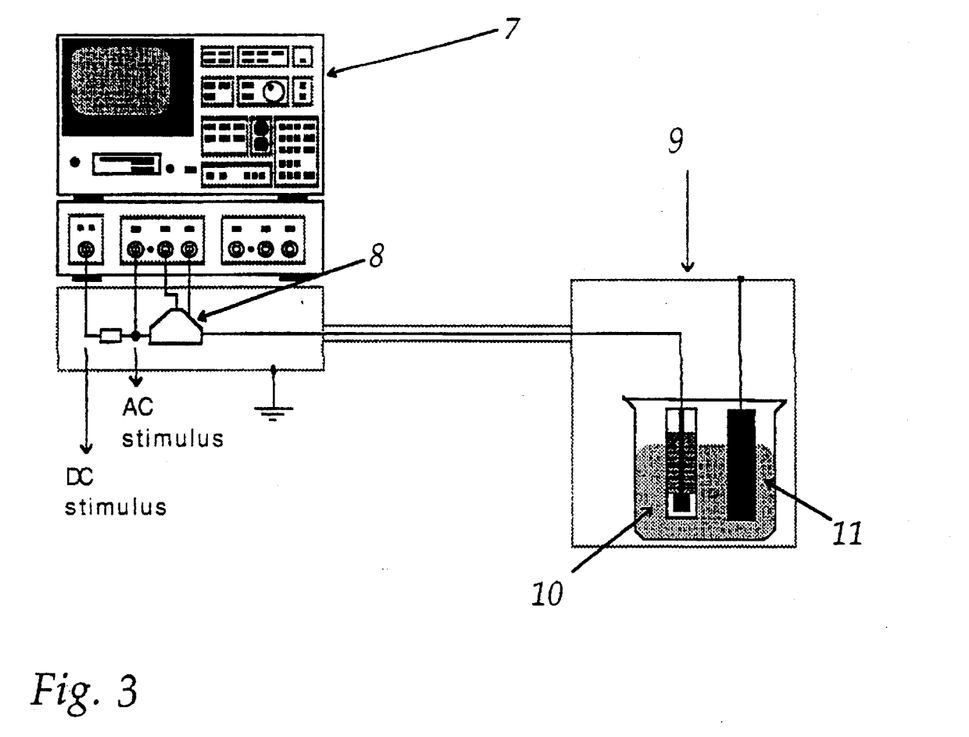
FIG. 3 shows the experimental system used for the AC impedance measurements with the compounds.

Electrochemical impedance measurements were carried out with a Hewlett Packard 4195A Network/Spectrum analyzer in the frequency range of 10 Hz till 100 kHz. Electrochemical measurement techniques are described in detail elsewhere [Bard A. J. and Faulkner L. R. "Electrochemical Methods, Fundamentals and Applications", John Wiley and Sons, New York 1980, pp. 316–369; MacDonald J. R. "Impedance Spectroscopy", John Wiley & Sons, New York 1987]. All measurements were done in an electrolyte solution containing 154 mM sodium chloride, 10 mM N-(2-hydroxyethyl)-piperazine-N'-(2-ethanesulfonic acid) (HEPES), 100 mM potassium-ferrocyanide and 100 mM potassiumferricyanide, buffered to a pH-value of 7.00 (HFC buffer). This electrolyte solution produces a very low electro-chemical impedance in the low-frequency region with gold electrodes. A two-electrode set-up was used as depicted in FIG. 3. The analyzer is denoted by 7, a signal divider by 8, a Faraday cage by 9 and the 9 mm$^2$ working electrode by 10. A blanc counter electrode 11 with a surface area of 100 mm$^2$, was used to minimise it's contribution to the measured membrane impedance.

Figure 4:
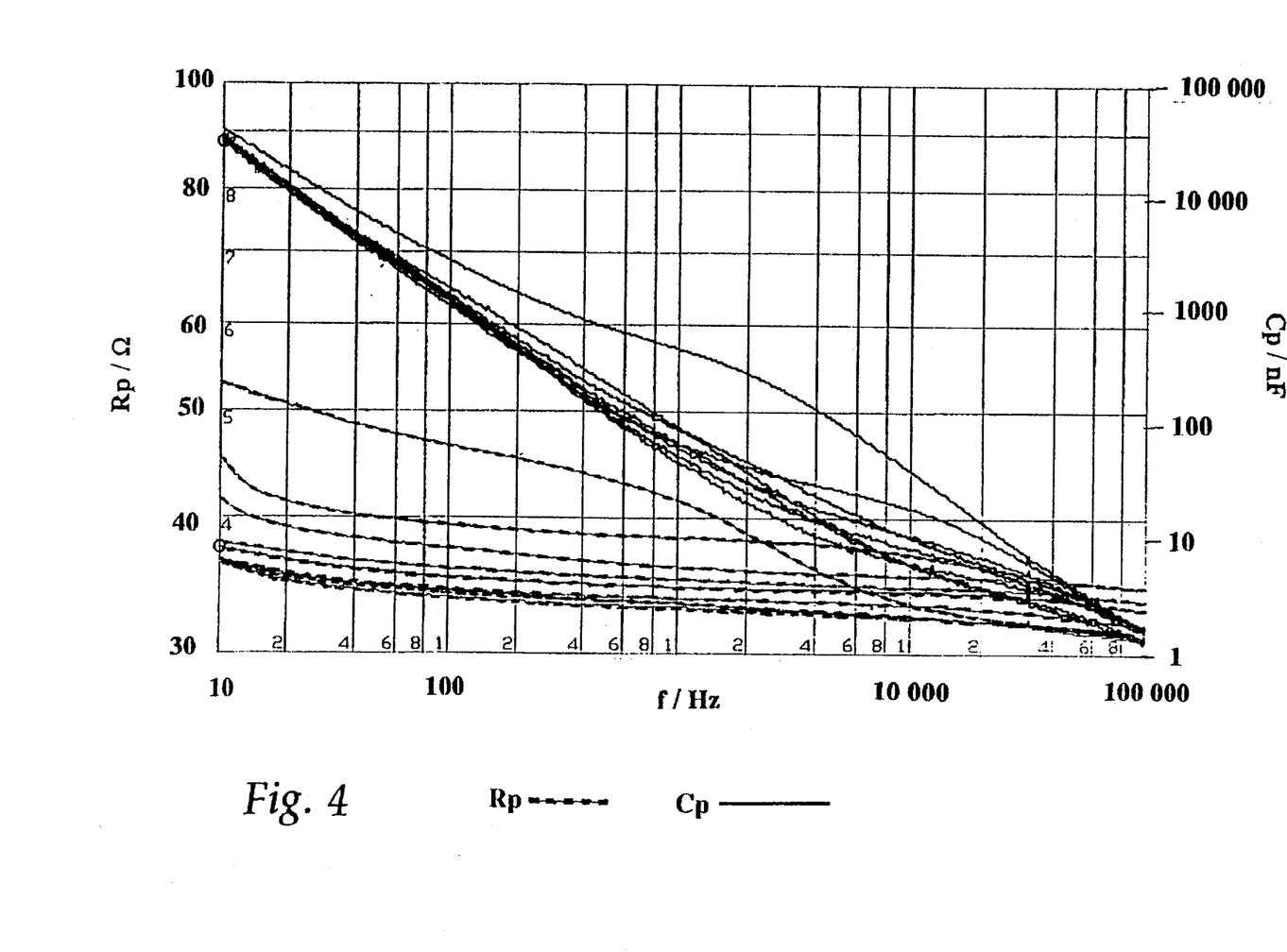
FIG. 4 shows the impedance spectra of eight untreated thin film gold electrodes.
Figure 5A:
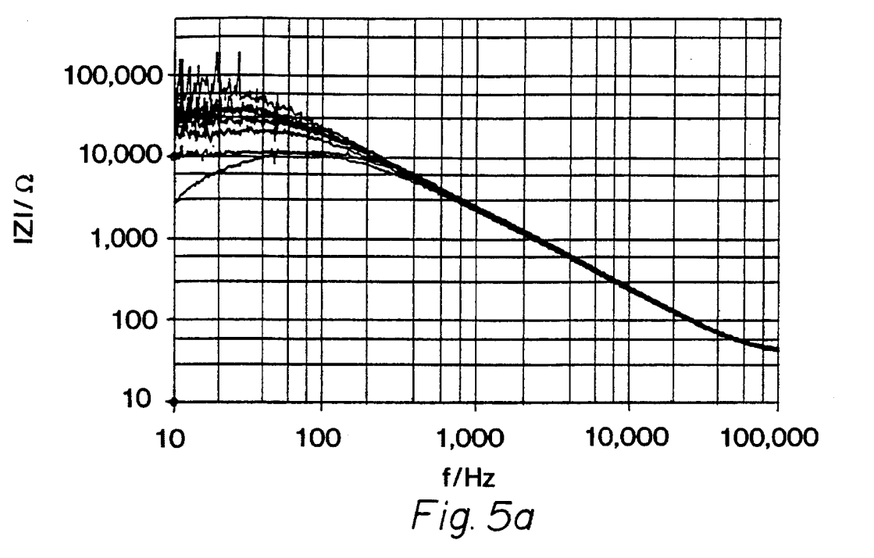
FIGS. 5a and 5b shows the impedance spectra of eight thin film gold electrodes coated with an insulating layer.
Figure 5B:
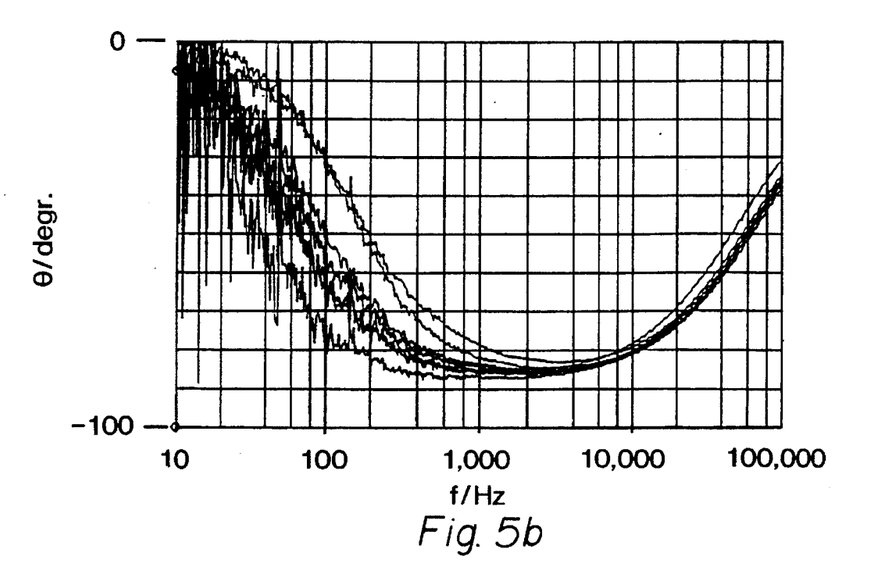

FIG. 4 shows the impedance spectra of 8 untreated electrodes. Data is represented in terms of apparent resistance Rp and capacitance Cp. It is observed that the resistance values of untreated gold electrodes are about 40 Ω or lower over the whole frequency range, while the capacitance steadily drops from high values (around 20 μF) at 10 Hz till low values (1.5 nF) at 100 kHz. FIG. 5a gives the modulus of the impedance, |Z|, after plasma treatment and subsequent coating with ODM. The impedance increases drastically at low frequencies, indicating blocking of the electro-chemical reaction. FIG. 5b gives the phase angle, θ, of the impedance, indicating largely capacitive properties of the electrode with a characteristic frequency at around 1 kHz.

Figure 6:
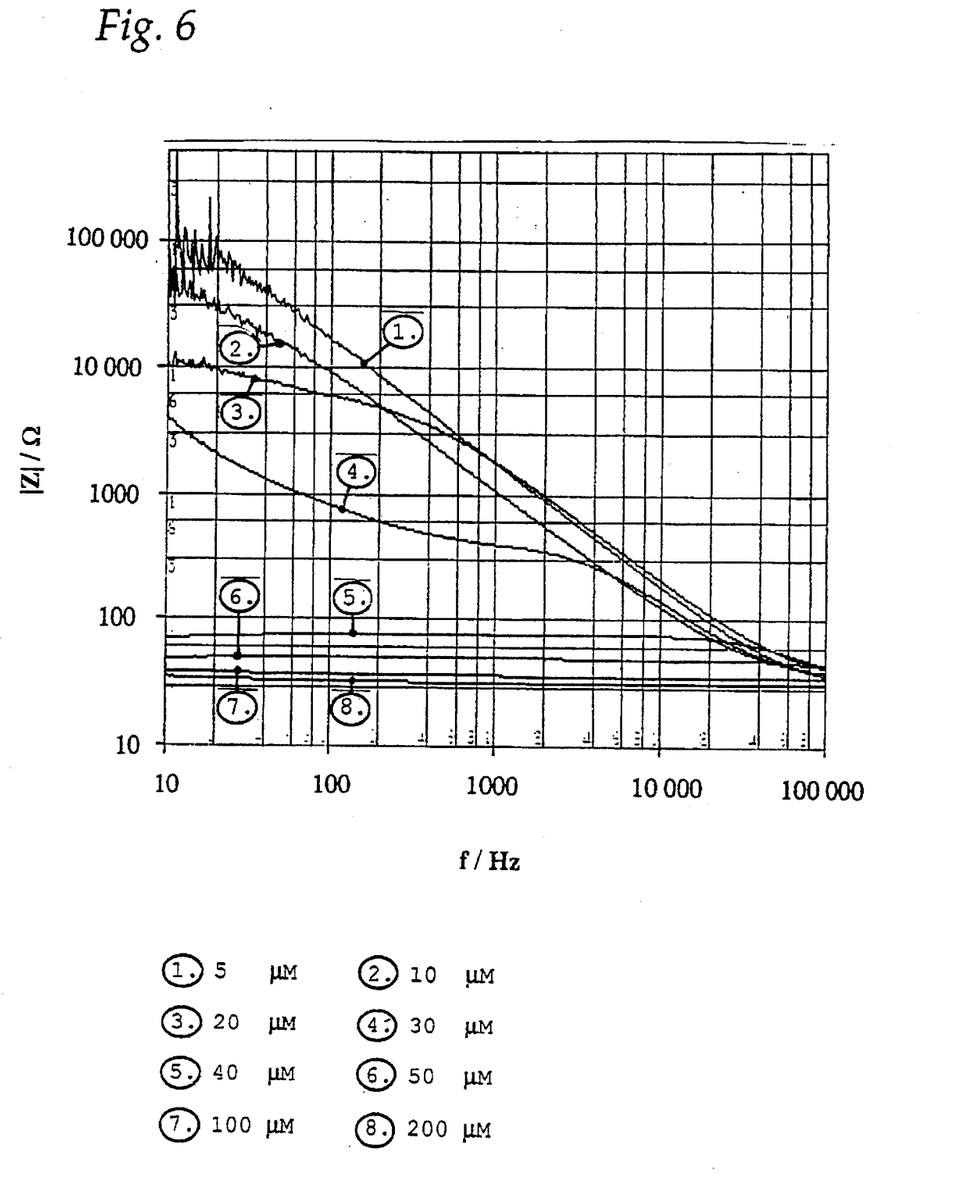
FIGS. 6 and 7 show the impedance spectra of insulating layer electrodes treated with the compounds according to the invention.
Figure 7:
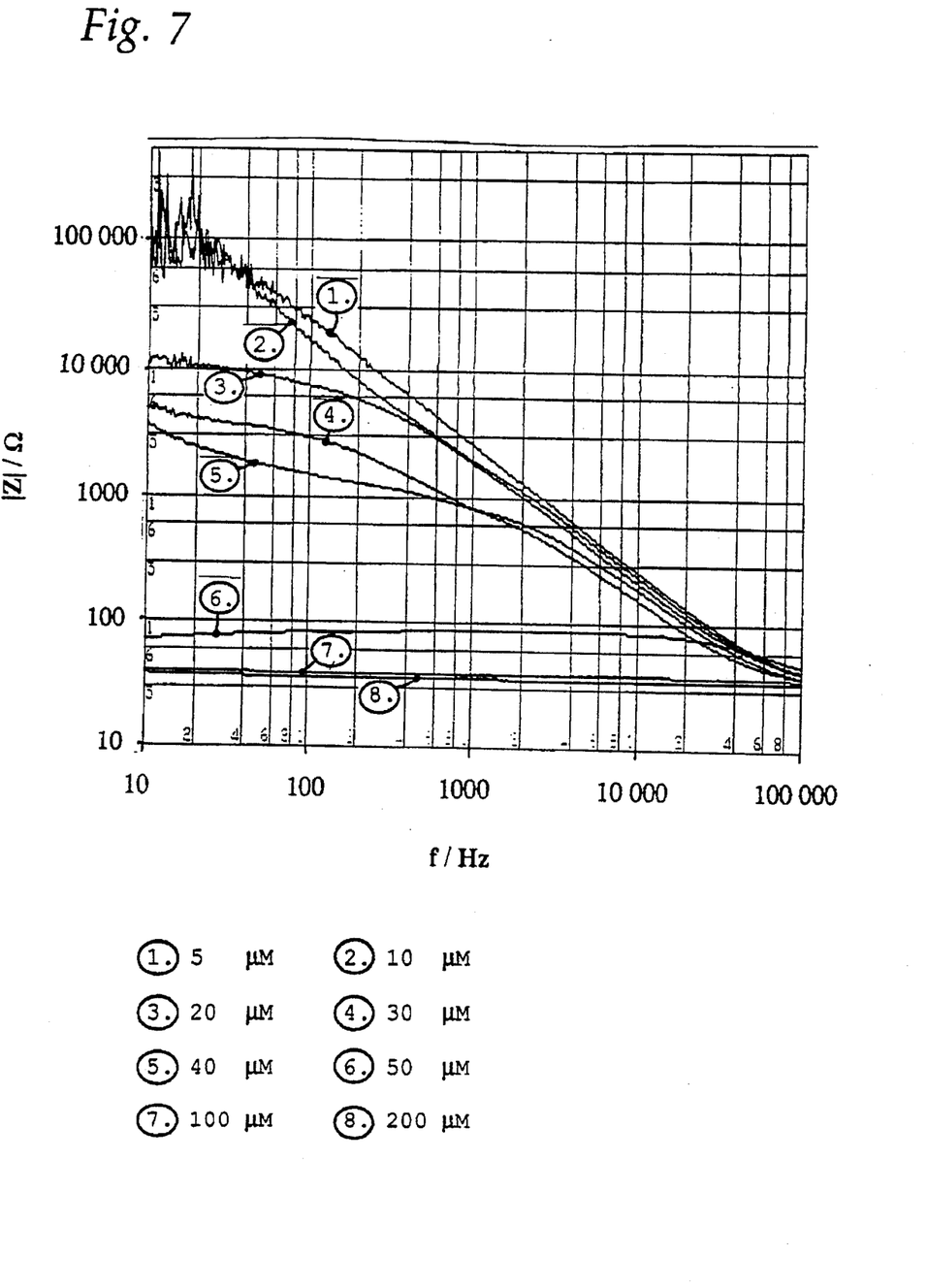

FIG. 6 gives the impedance characteristics, |Z| vs. frequency, of 7 ODM coated electrodes that have been immersed for 18 hours in ethanol solutions (1 ml) of MeIPT$_2$P at different concentrations (5–200 µM). It was observed that the treatment turns the electrode coating fully from the capacitive to the conductive state at concentrations above 30 µM of MeIPT$_2$P. The electrode impedance drops by a factor of 1000, fully restoring the conductivity to the level of that of an uncoated gold electrode. It was also observed that the strong hydrophobic character of the electrode surface was preserved. FIG. 7 shows the impedance characteristics of electrodes modified in the same fashion with (MeI)$_2$PT$_3$P.

Figure 8:
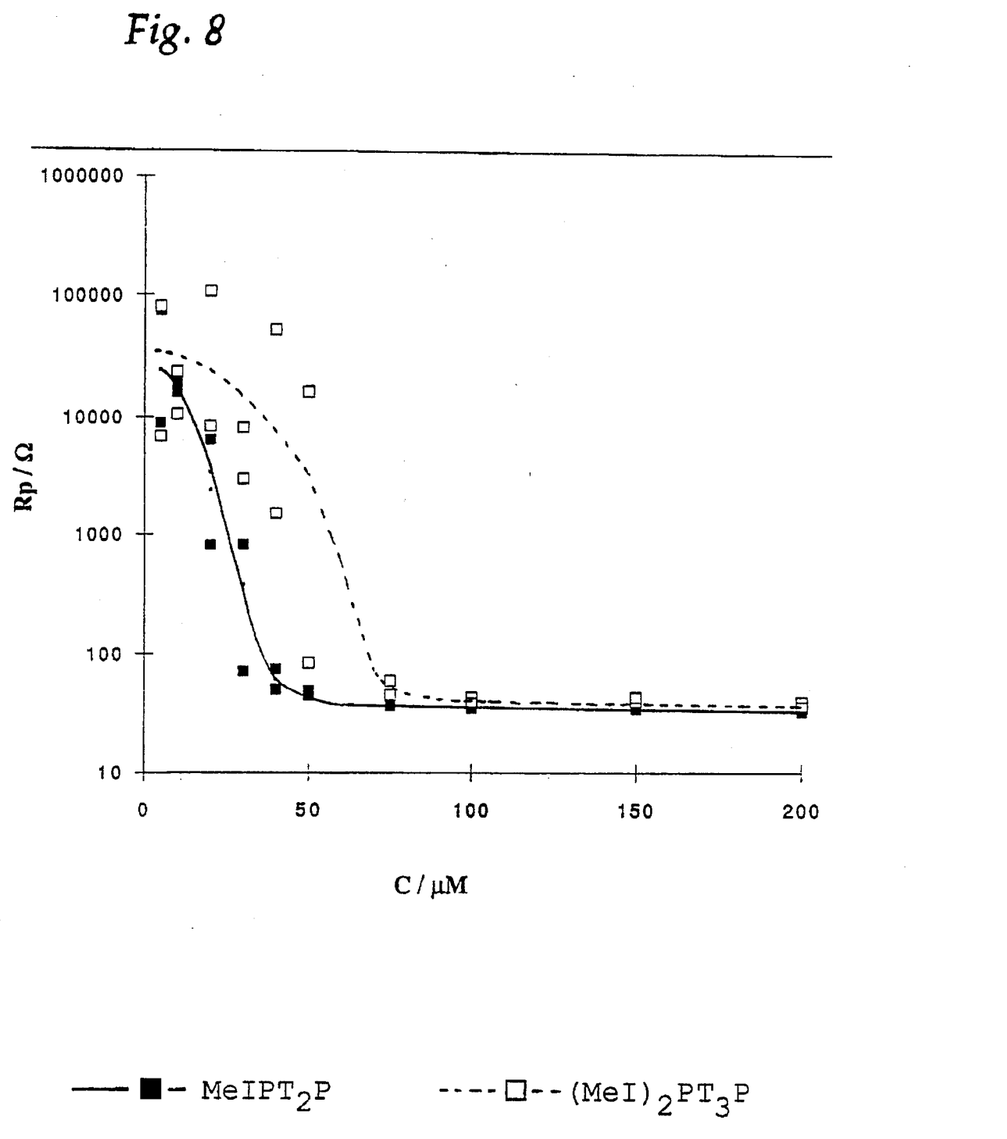
FIG. 8 shows the apparent resistance, $R_p$, vs. the concentration of the compounds according to the invention.
Figure 9:
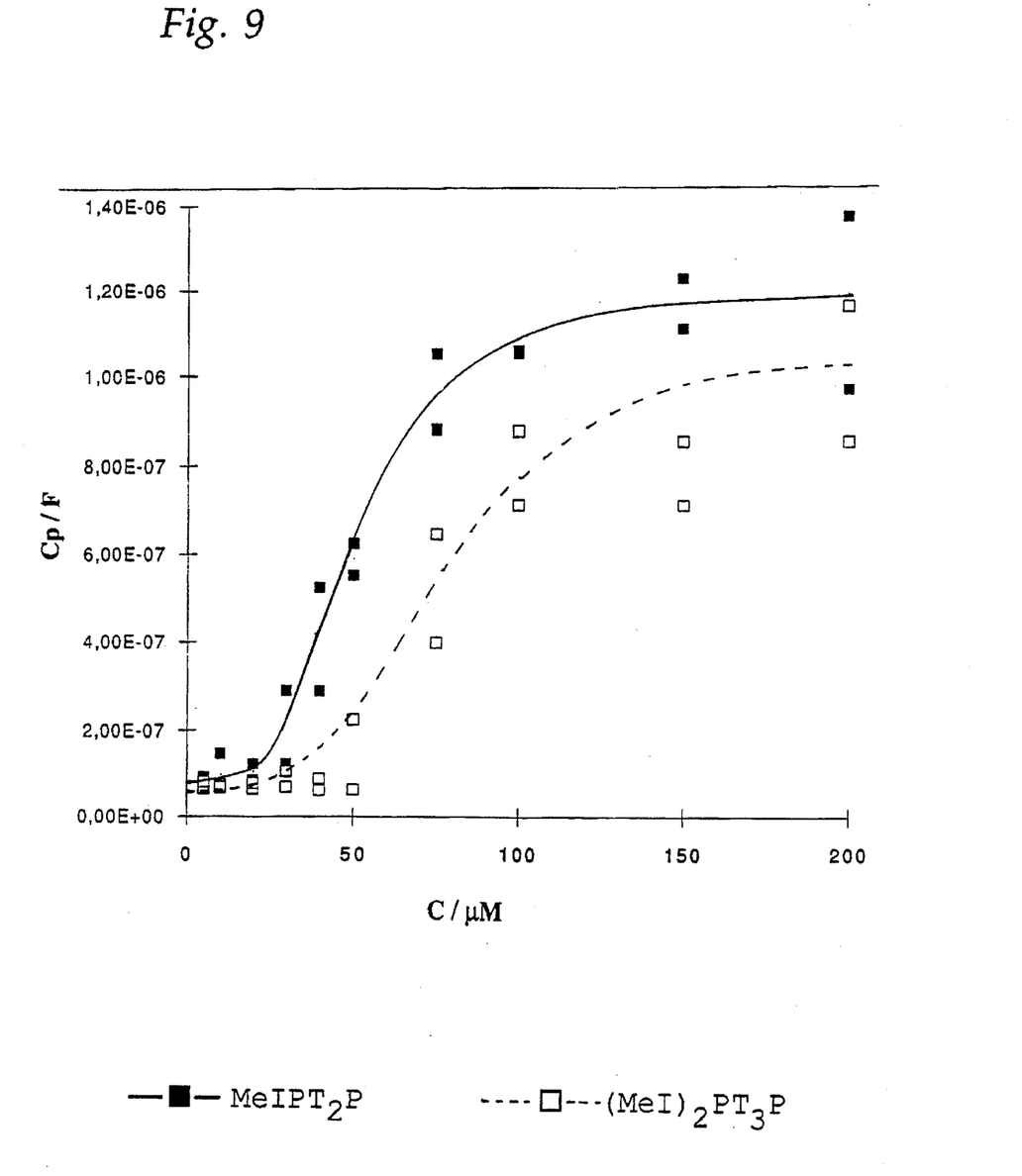
FIG. 9 shows the apparent capacitance, $C_p$, vs. the concentration of the compounds according to the invention.

FIG. 8 gives the change of Rp and FIG. 9 of Cp (at 100 Hz), as a function of concentration of both MeIPT$_2$P and (MeI)$_2$PT$_3$P. It is observed that the resistance drops and the capacitance rises with adsorption of the model thienoviologens to the ODM layer.

Conclusions

Although the underlying mechanism of conduction has not yet been elucidated fully at this stage, the data in FIGS. 6–9 clearly indicate that the "thienoviologens" according to the invention work as effective molecular conductors in a self-assembled molecular system. The changes of Rp and Cp with concentration are rather abrupt in a narrow concentration region (20–40 µM for MeIPT$_2$P and 30–50 for (MeI)$_2$PT$_3$P), and the changes are irreversible. A stable molecular assembly is thus formed at low concentrations from solution. The use of these compounds as molecular conductors is thus feasible and is of great importance in molecular electronics devices, such as electrochemical sensors or biosensors. The invention is, however, not restricted only to sensors, but may be used in all electronic devices where electron-conducting molecules are needed.

SYNTHESIS EXAMPLES

Reagents and Equipment

All used solvents were of analytical reagent grade. THF was dried on sodium and stored under dry argon. Diethylether was dried on anhydrous magnesium sulphate or molecular sieve 3 Å. Ethanol was dried on molecular sieve. 1,3-bis(diphenylphosphino)propane nickel(II) chloride, Ni(dppp)Cl$_2$ (Aldrich), was stored under argon at 4° C. 1,1'-bis(diphenylphosphino)ferrocene palladium(II) chloride, Pd(dppf)Cl$_2$ (Aldrich), in a 1:1 complex with dichloromethane, was used as received. 4-bromopyridine hydrochloride (Aldrich, 99%), ferrocenecarboxaldehyde (Aldrich, 98%), methyliodide (Aldrich), 2-bromothiophene (Janssen Chimica, 98%), 2,5-dibromothiophene (Aldrich, 95%), hydrazinc hydrate (Aldrich, 98%), sodium periodate (Merck, p.a.), iodine (Merck, doubly sublimated), bromine (J. T. Baker), magnesium shavings (Merck) and n-butyllithium (Aldrich, 1.6M solution in hexanes) were used as provided. Molecular sieves were always heated with a bunsen burner in a roundbottom flask under vacuum for about 15 minutes. All reactions with magnesium, butyllithium, Ni(dppp)Cl$_2$, Pd(dppf)Cl$_2$ and palladium-amalgam were conducted under dry argon delivered by a Schlenck apparatus.

Elemental analysis was carried out by Mikroanalytisches Labor Pascher (Remagen, Germany). Proton NMR spectra were acquired on a Broker WM 300 FT-NMR spectrometer at 300 MHz, or on a Jeol JNM-FX200 FT-NMR spectrometer at 200 MHz. Mass spectra were recorded on a Finnigan MAT TSQ-70 quadrupole mass spectrometer, equiped with a 59980 Å particle beam interface (Hewlett Packard). The spectra were recorded in EI impact mode, using an electron energy of 70 eV. The samples, dissolved in methanol, were introduced by means of an LC/MS system in column bypass mode (FIA), using a flow rate of 0.5 ml/min. In some cases the sample was introduced by slowly heating the solid from a probe.

Thiophene Oligomers

2,2'-bithiophene, T$_2$

The Grignard reagent 2-thienylmagnesiumbromide (T-MgBr) was made from 2-bromothiophene (T-Br) in a standard fashion in a three-necked roundbottom flask with 9 gr (370 mmol) of magnesium and 45 gr (276 mmol) of T-Br in 120 ml diethylether. Initially, a small amount of ether and a few milliliters of T-Br were added to the magnesium and the reaction was initiated by crushing some of the magnesium with a glass rod. The reaction was maintained by adding the rest of the T-Br and the ether in small portions from a dropping funnel. The Grignard reagent was refluxed for an additional half hour. In a separate, three-necked roundbottom flask was placed 120 ml of ether, 37.5 gr (230 mmol) of T-Br and 180 mg (0.33 mmol) of Ni(dppp)Cl$_2$. The Grignard reagent was then added slowly, under a steady outflow of argon. The mixture was refluxed and stirred for 3 hours and 15 minutes and poured on ice with dilute hydrochloric acid. The product was then extracted with ether. After drying the ether layer on anhydrous magnesium sulphate, the organic layer was filtrated and the ether evaporated. The residue was redissolved in warm methanol. Some water was added to the methanol, while still warm, until a yellow precipitate started to form. The mixture was then put overnight at 4° C. to form yellow crystals. After filtration and drying in vacuo the product was molten and poured in a dry storage vessel. Yield: yellow crystals of T$_2$, 25.16 gr (152 mmol, 66%). M.p.: 31° C. (litt.: 33). Elemental analysis: found% (theory%) C 57.54 (57.79), H 3.61 (3.64), S 38.0 (38.6). $^1$H-NMR (300 MHz, CDCl$_3$,): ∂=7.21 (2H, dd, H=5.0 and 1.2 Hz), ∂=7.01 (2H, dd, J=5.0 and 3.6 Hz), ∂=7.18 (2H, dd, J=1.2 and 3.6 Hz). M/z (Mass peak from mass spectrometry): 166 D (M.W.=166), small impurity at 248 D, probably 2,2':5',2"-terthiophene (M.W.=248).

2,2':5',2"-terthiophene, T$_3$ 13.16 gr (81 mmol) of T-Br was allowed to react with 25 gr (103 mmol) of magnesium in about 30 ml of ether and the formed Grignard reagent was refluxed for one additional hour. The reagent was then added slowly to a stirred solution of 7.25 gr (30 mmol) of 2,5-dibromothiophene (Br-T-Br) and 160 mg (0.3 mmol) of Ni(dppp)Cl$_2$ in 40 ml of dry THF. The mixture was refluxed for 3 hours. The reaction mixture was poured on ice with dilute hydrochloric acid and the aqueous layer extracted with hexane. The organic layer was dried and the solvent evaporated. The product was obtained by a first crystallization from hexane and a second crystallization from ethanol and finally dried in vacuo. Yield: 1.58 gr orange powder of T$_3$ (6.4 mmol, 21%). M.p. 80°–81° C. (litt.: 94). Elemental analysis: found % (theory %) C 57.44 (58.03), H 3.22 (3.25), S 38.0 (38.7). $^1$H-NMR (300 MHz, CDCl$_3$): ∂=7.22 (2H, dd, J=5.3 and 1.2 Hz), ∂=7.17 (2H, dd, J=3.7 and 1.2 Hz), ∂=7.08 (2H, s), ∂=7.02 (2H, dd, J=5.3 and 3.7 Hz). M/z: 248 D (M.W.=248) very small impurity at 330 D, probably 2,2':5',2":5",2'"-quaterthiophene, T$_4$.

5,5'-dibromo-2,2'-bithiophene, Br-T$_2$-Br 10 gr (60 mmol) of T$_2$, in a three-necked roundbottom flask, was dissolved in 200 ml dry, THF and cooled in an acetone bath till −78° C. with liquid nitrogen. 95 ml of butyllithium (BuLi) (152 mmol) was added with a glass syringe and the mixture stirred at −78° C. for 1.5 hours. 9 ml (27.9 g, 174 mmol) of bromine was added dropwise from a glass pipette. The reaction mixture was further stirred at −78 ° C. for 1 hour and, after warming, still stirred for 1 hour at room temperature. The reaction mixture was then quenched with dilute hydrochloric acid and the product extracted with THF and hexane. After drying the organic layer on anhydrous magnesium sulphate, the solvents were evaporated and the product recrystallized from a mixture of ethanol and THF as an orange powder. The product was dried in vacuo. Yield: 11.71 gr (36 mmol, 60%) of Br-T$_2$-Br. M.p. 141° C. (litt.: 143). Elemental analysis: found% (theory%) C 28.77 (29.65), H 1.18 (1.24), S 18.5 (19.79), Br 52.0 (49.31). $^1$H-NMR. (200 MHz, CDCl$_3$): ∂=6.95 (2H, d, J=3.8 Hz), ∂=6.83 (2H, d, J=3.8 Hz). M/z: 324 D (M.W.=324).

2,2':5',2":5",2'"-quaterthiophene, T$_4$

Thienylmagnesiumbromide, made from 13 gr (80 mmol) of T-Br and 2.43 gr (100 mmol) of magnesium in 50 ml of anhydrous ether, was added to a solution of 11.71 gr (36 mmol) of 5,5'-dibromo-2,2'-bithiophene and 100 mg (0.18 mmol) of Ni(dppp)Cl$_2$ in 150 ml of ether. The reaction mixture was refluxed for 4 hours and subsequently poured on an ice/dilute hydrochloric acid mixture. The product was extracted with toluene and recrystallized from a mixture of toluene and ethanol. The resulting orange powder was dried in vacuo. Yield: 6,75 gr (20 mmol, 57%) of T$_4$. M.p.: 203° C. (litt: 212). Elemental analysis: found% (theory%) C 56.49 (58.15), H 3.05 (3.05), S 37.0 (38.8). $^1$H-NMR (300 MHz, CDCl$_3$): ∂=7.23 (2H, dd, J=5.0 and 1.0 Hz), ∂=7.19 (2H, dd, J=3.7 and 1.0 Hz), ∂=7.08 (4H, s), ∂=7.03 (2H, dd, J=5.0 and 3.7 Hz). M/z: 330 D (M.W.=330).

5,5"-dibromo-2,2',5',2"- terthiophene, Br-T$_3$-Br 1.0 gr (4 mmol) of T$_3$ was brominated with the same procedure as T$_2$ by reaction with 8.9 mmol of butyllithium and 9 mmol of bromine at −78° C. The product was extracted with ether, crystalized from toluene/ethanol and dried in vacuo, yielding an orange/brown powder. Yield: 830 mg (2 mmol, 50%) of Br-T$_3$-Br. M.p.: 151° C. (litt.: 160). Elemental analysis: found% (theory%) C 35.60 (35.49), H 1.65 (1.49), S 23.2 (23.7), Br 38.0 (39.3). $^1$H-NMR (300 MHz, CDCl$_3$): ∂=7.00 (2H, s), ∂=6.98 (2H, d, J=3.8 Hz), ∂=6.91 (2H, d, J=3.8 Hz). M/z: 406 D (M.W.=406).

5,5'"-dibromo-2,2':5',2":5",2'"-quaterthiophene, Br-T$_4$-Br 6 gr 18 mmol) of T$_4$ in 100 ml THF was brominated by reaction with BuLi (23 ml, 36 mmol) at −78° C. for 2 hours and bromine (2 ml, 39 mmol) at −78° C. for 1 hour, followed by stirring one hour at room temperature. After quenching the reaction mixture with aqueous HCl, the product was isolated by filtration and washing the resulting yellow solid with THF, methanol and ethanol Yield: 11.63 gr Br-T$_4$-Br (24 mmol, 132%, probably containing adsorbed solvent.).

M.p. 245° C. Elemental analysis: found% (theory%) C 38.12 (39.36), H 1.88 (1.65), S 25.1 (26.3), Br 32.2 (32.73), Mg<0.1. $^1$H NMR (300 MHz, CDCl$_3$): ∂=7.06 (2H, d, J=3.8 Hz), ∂=7.01 (2H, d, J=3.8 Hz), ∂=6.98 (2H, d, 3.8 Hz), ∂=6.91 (2H, d, J=3.8 Hz). M/z: 488 D (M.W.=488), impurities present at 408 D (T$_4$-Br), 330 D (T$_4$), 324 D (Br-T$_2$-Br), 248 D (T$_3$).

Pyridylthiophenes 4-bromopyridine, P-Br

Since 4-bromopyridine (P-Br) is not very stable (Wibaut J. P., 1955), the compound was freshly prepared prior to each coupling reaction. Initially, the free base was obtained from the commercially available hydrochloride by adding a strong ammonia solution to the solid compound, and, after stirring, directly drying the separating liquid over a 1:1 mixture of anhydrous magnesium sulphate and sodium bicarbonate. The bee base thus obtained could be stored under Argon at −15° C. without any notice of polymerization in one week. The yield was, however, low with this procedure (approx. 50%). A better yield of P-Br was obtained by reacting the hydrochloride with an equimolar amount of aqueous sodium hydroxide and extracting the free base into hexane. The solvent was then removed slowly on a rotation evaporator, taking care not to evaporate the P-Br. The preparation, obtained by the latter method, was then directly used in the coupling reaction.

2-(4-pyridyl)thiophene, PT

To a 500 ml three-necked roundbottom flask was added 200 ml dry THF, 0.54 gr (1 mmol) Ni(dppp)Cl$_2$ and 87 mmol of P-Br, fleshly prepared from 17 gr of the hydrochloride. To this was added T-MgBr, prepared from 14 gr (87 mmol) of T-Br and 2.5 gr (103 mmol) of magnesium. The mixture was refluxed for 20 hours and subsequently quenched with aqueous ammoniumchloride/HCl. About 100 ml of hexane was added and the organic layer extracted three times with dilute hydrochloric acid. Hereafter, the water layers were combined and made mildly alkaline with a strong sodium hydroxide solution. The product was extracted with three portions of 100 ml of chloroform. The chloroform solution was boiled shortly with a small amount of active coal and filtrated, whereafter the chloroform was removed on a rotation evaporator. Trituration of the remaining brown solid in boiling hexane yielded a clear yellow solution and a black unsoluble residue. After decanting the yellow solution, the solvent was evaporated and the remaining yellow solid dried in vacuo. The product was once recrystallized from 100 ml of hexane (a few hours standing at room temperature and overnight standing at 4° C.). The resulting yellow crystals were filtrated off, washed with cold pentane twice and dried in vacuo, (fraction I). From the collected pentane supernatants a second fraction of product with a lesser purity was obtained, by evaporating the solvent on a rotation evaporator and drying the remaining solid in vacuo. Yield: fraction I: light yellow powder of PT, 3.88 gr (24 mmol, 28%), fraction II: yellow powder of PT 6.00 gr (37.2 mmol, 43%), still containing some P-Br. M.p. (fraction I): 90°–91° C. (litt.: 92.5°–93.5° C.). Elemental analysis: found% (theory%) C 66.87 (67.05), H 4.38 (4.38), N 8.90 (8.69), S 18.7 (19.9). $^1$H-NMR (300 MHz, CDCl$_3$): ∂=8.59 (2H, dd, J=4.6 and 1.7 Hz), ∂=7.52 (1H, dd, J=3.8 and 1.1 Hz), ∂=7.49 (2H, dd, J=4.6 and 1.7 Hz), ∂=7.43 (1H, dd, J=5.0 and 1.1 Hz), ∂=7.14 (1H, dd, J=3.8 and 5.0 Hz). M/z: 161 D (M.W.=161).

2-(4-pyridyl)-5-bromothiophene, PT-Br 9.88 gr (61 mmol) of PT was dissolved in 150 ml THF and the mixture cooled in an acetone bath fill −80° C. with liquid nitrogen. 40 ml of BuLi was added and the mixture stirred for 1 hour in which the temperature was allowed to rise till −50° C. The reaction mixture was stirred for an additional 2 hours at −50° C. A solution of 10 gr bromine in 50 ml of THF was slowly added and the mixture stirred for 1 hour at −50° C. The acetone bath was then removed and the mixture stirred overnight at room temperature. Hereafter, the reaction mixture was poured into 200 ml dilute hydrochloric acid solution. The aqueous layer was separated and the organic layer twice extracted with an additional 100 ml of hydrochloric acid. The collected acid fractions were then neutralized by the slow addition of strong sodiumhydroxide solution while stirring. The formed precipitate was then extracted from the solution with three portions of 100 ml chloroform. The chloroform layer was dried on magnesium sulphate, boiled with a small mount of active coal and filtrated. The chloroform was then evaporated. Residual pyridylthiophene was dissolved in boiling hexane and acetone, giving 2.18 gr yellow/brown powder consisting of 12% PT and 88% PT-Br ($^1$H-NMR). $^1$H-NMR of PT-Br (300 MHz, CDCl$_3$): $\partial$=8.59 (2H, dd, J=4.5 and 1.6 Hz), $\partial$=7.38 (2H, dd, J=4.5 and 1.6 Hz), $\partial$=7.26 (1H, d, J=3.8 Hz), $\partial$=7.10 (1H, d, J=3.9 Hz). M/z: 239, 241 D (M.W.=240.1)

2,5-di(4-pyridyl)-thiophene, PTP

A Grignard reagent was prepared from 2,42 gr 10 mmol) 2,5-dibromothiophene and 0.5 gr magnesium in about 100 ml of ether. The reagent separated as a darkbrown oil layer from the ether. After an additional 1.5 hours stirring with a teflon magnetic stirring bar, the reagent was added to a mixture of 3.56 gr of freshly prepared 4-bromopyridine in about 100 ml THF and a small amount (10 mg) of Ni(dppp)Cl$_2$. The mixture was refluxed overnight (18 hours). Succesive acid and alkaline extractions, as with 2-(4-pyridyl)thiophene, yielded 140 mg of an orange powder, soluble in chloroform, which appeared to be a complex mixture. Also a red, unsoluble powder was obtained as a side-product (likely polythiophene). A fraction of the reaction mixture was run on a TLC plate with acetone as the eluent. Six bands appeared, from which the the 5th band, with a green fluorescence, could be identified as PTP by NMR. $^1$H-NMR (200 MHz, CDCl$_3$): $\partial$=8.64 (2H, dd, broad), $\partial$=7.54 (1H, s), $\partial$=7.51 (2H, dd, J=4.6 and 1.6 Hz).

2-(4-pyridyl)-5-iodothiophene, PT-I

To 100 ml of 80% acetic acid in water was added 5 gr (31 mmol) PT, 6.9 gr (27 mmol) iodine and 4.1 gr (18 mmol) periodic acid dihydrate. The mixture was heated at 80° C. overnight (18 hrs). After cooling on an ice bath, the product was filtrated, recrystalized from chloroform and dried in vacuo. Yield: 5.3 gr yellow/brown powder (18 mmol, 58%). Elemental analysis: found% (theory%) C 20.59 (37.65), H 1.17 (2.11), N 2.87 (4.88), S 6.70 (11.2), I 68.8 (44.2), 1 mole equivalent of I$_2$ present as impurity. $^1$H-NMR (300 MHz, CDCl$_3$): $\partial$=8.60 (2H, dd, J=4.7 and 1.6 Hz), $\partial$=7.39 (2H, dd, J=4.5 and 1.7 Hz), $\partial$=7.29 (1H, d, J=3.8 Hz), $\partial$=7.17 (1H, d, J=3.8 Hz). M/z: 287 D (M.W.=287.1)

5-(4-pyridyl)-2,2'-bithiophene, PT$_2$

T-MgBr, prepared from 0.3 gr magnesium and 1.0 gr T-Br in 10 ml of ether, was added to a mixture of 33 mg Ni(dppp)Cl$_2$ and 1.445 gr of PT-Br in 50 ml of THF. The mixture was refluxed for 18 hrs. The working-up procedure was initially the same as that of PT-Br, products being first extracted with dilute hydroclorlic acid and then from slightly alkaline solution back to chloroform. The chloroform was evaporated and the resulting mixture triturated with warm hexane to yield two fractions: fraction I, soluble in hexane and chlorofrom; fraction II, soluble in chloroform but not in hexane. NMR-analysis of the reaction mixture after 2 hrs indicated the presence of PT, PT-Br and PT$_2$, after 20 hrs the peaks of PT$_2$ were only slightly increased in favour of the PT$_2$. Fraction I was a mixture of PT, PT-Br and PT$_2$, with relatively more PT. Fraction II (600 mg) contained PT-Br (40%), PT (7%) and PT$_2$ (53%) on basis of the $^1$H-NMR-spectrum. $^1$H-NMR of PT$_2$ (300 MHz, CDCl$_3$): $\partial$=8.59 (2H, dd, broad), $\partial$=7.46 (2H, dd, broad), $\partial$=7.43 (1H, d, J=3.9 Hz), $\partial$=7.28 (1H, dd, J=1.1 and 5.1 Hz), $\partial$=7.25 (1H, dd, J=1.1 and 3.9 Hz), $\partial$=7.19 (1H, d, J=3.8 Hz), $\partial$=7.05 (1H, dd, J=3.6 and 5.1 Hz).

5,5'-bi(4-pyridyl)-2,2'-bithiophene, PT$_2$P

In 40 ml of 50% methanol in water was dissolved 3.6 gr (90 mmol) of sodium hydroxide 5.166 gr 18 mmol of PTI and 540 mg (10.8 mmol) of hydrazine hydrate. After stirring the solution, a solution of 240 mg (0.9 mmol) of palladium chloride and 244 mg (0.9 mmol) of mercuric chloride in water (with some KCl) were added. The mixture was refluxed overnight (18 hrs). The reaction mixture was then cooled and the palladium-amalgam with the product filtrated on a glass filter. The residue was washed with water and the product dissolved from the amalgam with some acetone and portions of chloroform. The organic layers were collected together and the solvents evaporated. In order to remove water, the residue was shaken with 250 ml of methanol, after which the methanol was evaporated. The dry residue was then shaken with hexane, filtered off on a glass filter, washed with hexane to remove PT and washed with pentane. The product was dried in air. Yield: 1.4 gr (4.4 mmol, 49%) of yellow/brown powder. 1.0 gr of the product was sublimed at 230°–250° C. yielding 898 mg of PT$_2$P. M.p. 240° C. (litt. 241°–242° C.). Elemental analysis: found% (theory%) C 66.89 (67.47), H 3.80 (3.77), N 8.75 (8.74), S 19.6 (20.0). $^1$H-NMR (300 MHz, CDCl$_3$): $\partial$=8.62 (4H, dd, J=4.6 and 1.6 Hz), $\partial$=7.47 (4H, dd, J=4.5 and 1.7 Hz), $\partial$=7.46 (2H, d, J=3.9 Hz), $\partial$=7.27 (2H, dd, J=4.1 Hz). M/z: 320 D (M.W.=320.44).

5,5"-bi(4-pyridyl)-2,2':5',2"-terthiophene, PT$_3$P (CuCl$_2$ method)

PT$_2$ Fraction II (600 mg), being a mixture of nearly 1:1 of PT$_2$ and PT-Br was dissolved in about 50 ml of THF and the solution cooled to −60° C. on an acetone bath with liquid nitrogen. 0.8 ml BuLi was added and the mixture stirred for 1 hr, the temperature rising slowly till −30° C. 160 mg of anhydrous CuCl$_2$ was added in small portions, while stirring at −30° C., followed by stirring for an additional hour at −30° C. The reaction mixture was then warmed till room temperature and stirred for an additional 4 hrs. The mixture was subsequently poured in dilute hydrochloric acid, forming a red precipitate. The precipitate was filtered off and washed with water. The red precipitate was then washed with a strong ammonia solution, dating which the color of the precipitate changed to orange/brown. The precipitate was rinsed resp. with methanol, ether and hexane and air-dried. Yield: 17 mg of orange powder. Elemental analysis: found% (theory%) C 61.13 (65.64), H 3.38 (3.51), N 6.10 (6.96), S 23.1 (23.9). $^1$H-NMR (200 MHz, CDCl$_3$): $\partial$=8.60 (4H, dd, J=4.1 and 1.6 Hz), $\partial$=7.47 (4H, dd, J=4.5 and 1.6 Hz), ∂=7.46 (2H, d, J=3.3 Hz), ∂=7.22 (2H, d, J=4.1 Hz), ∂=7.19 (2H, s). M/z 243 (Br-T-Br?), 320 (PT$_2$P), 402 (PT$_3$P).

5,5"-bi(4-pyridyl)-2,2':5',2"-terthiophene, PT$_3$P (Ni(dppp)Cl$_2$ method)

1.61 gr (10 mmol) PT was dissolved in a mixture of 100 ml diethylether and 25 ml THF. The solution was cooled on an acetone bath till −78° C. with liquid nitrogen. 6.25 ml BuLi was added, followed by stirring for 1 hr. 1.85 gr of anhydrous MgCl$_2$ was added at a temperature of −60° C. and the mixture was stirred for 2 hrs, during which the mixture slowly attained room temperature. A black tar formed at the bottom of the flask during the stirring. In a separate flask 1 gr (4 mmol) of Br-T-Br and 50 mg of Ni(dppp)Cl$_2$ were dissolved in 100 ml THF and 100 ml diethylether. The Grignard reagent was transferred, with a spatula, to this mixture (2-pot reaction). The coupling reaction proceeded under continuous stirring under reflux for 20 hrs. Due to the difficulties in handling the Grignard reagent, a second reaction was performed exactly the same way, but the mixture of Br-T-Br, Ni(dppp)Cl$_2$, ether and THF were added to the Grignard reagent (1-pot preparation). Differences in the results were not noticed. Reaction products were extracted from the mixture first by extraction of the organic layer with dilute hydrochloric acid and, after making the pooled aqueous layer slightly alkaline, back extracted with chloroform. Three fractions were obtained: fraction I, soluble in chloroform and hexane; fraction II, soluble only in chloroform and not in hexane; fraction III, a residue not soluble in chloroform and hexane. Fraction I contained largely PT ($^1$H-NMR). Fraction II contained PT$_2$P and some PT$_3$P (by $^1$H-NMR and Mass spectrometry). Only from the second trial, the 1-pot method, a very small amount of PT$_3$P could be isolated, with column chromatography (silica column with chloroform as eluent): $^1$H-NMR (300 MHz, CDCl$_3$): ∂=8.61 (4H, dd, broad), ∂=7.46 (4H, dd, J=3.8 and 1.6 Hz), ∂=7.45 (2H, d, J=3.7 Hz), ∂=7.22 (2H, d, J=3.9 Hz), ∂=7.19 (2H, s).

5,5'''-bi(4-pyridyl)-2,2':5',2":5",2'''-quaterthiophene, PT$_4$P (Ni(dppp))Cl$_2$ method)

A Grignard reagent was prepared from 3.25 gr. of PT (20 mmol), 12.5 ml BuLi and 3.68 gr. MgCl$_2$ in 100 ml THF as with PT$_3$P. BuLi was only added at a higher temperature: −45° C. To the PT-MgBr was added 3.24 gr Br-T$_2$-Br (10 mmol), 100 mg Ni(dppp)Cl$_2$ and 100 ml THF and the mixture was stirred and refluxed for 20 hrs. The products were isolated in the same way as the PT$_3$P. The fraction that dissolved in chloroform and not in hexane was further analyzed. With mass-spectrometry peaks appeared at 320 D (PT$_2$P), 325 D (PT$_3$?), 405 D (PT$_3$-Br) and 484 D (PT$_4$P), while $^1$H-NMR revealed the presence of PT$_2$P and PT$_3$-Br. In an other trial, at 16 millimolar scale, similar results were obtained: only PT$_2$P and PT$_3$-Br could be identified by $^1$H-NMR. $^1$H-NMR of PT$_3$-Br (300 MHz, CDCl$_3$): ∂=8.60 (d, broad, overlap with PT$_2$P), ∂=7.46 (d, broad, overlap with PT$_2$P), ∂=7.45 (d, J=3.8 Hz), ∂=7.21 (d, J=3.9 Hz), ∂=7.14 (d, J=3.7 Hz), ∂=7.02 (d, J=3.9 Hz), ∂=6.98 (d, J=3.8 Hz).

5,5'''-bi(4-pyridyl)-2,2':5',2":5",2'''-quaterthiophene, PT$_4$P (CuCl$_2$ method)

1.61 gr. PT (10 mmol) and 0.83 gr. T$_2$ (5 mmol) were dissolved in 100 ml THF and the solution cooled to −70° C. 12.5 ml BuLi (20 mmol) were added at −60° C. and the reaction allowed to proceed for 2 hrs, slowly rising the temperature from −60 till −45° C. To this a solution of 2.1 gr. anhydrous CuCl$_2$ in 100 ml THF was added. The cooling bath was removed and the mixture was stirred overnight at roomtemperature. The product of the reaction was again extracted with dilute HCl, the acid was neutralized with strong ammonia and the products extracted in chloroform. Again the fraction soluble in chloroform, but not soluble in hexane, was further analyzed. $^1$H-NMR indicated the presence of mainly PT$_2$P and some PT$_4$P besides other, still unidentified, compounds. $^1$H-NMR of PT$_4$P (300 MHz, CDCl$_3$): ∂=8.61 (dd, overlap with PT$_2$P), ∂=7.46 (dd, overlap with PT$_2$P), ∂=7.44 (d, J=3.9 Hz), ∂=7.19 (d, J=4.0 Hz), ∂=7.15 (d, J=3.7 Hz), ∂=7.11 (d, J=3.8 Hz).

Reactions with ZnCl$_2$ and Pd(dppf)Cl$_2$ 1.61 gr. of PT (10 mmol) was dissolved in 100 ml THF and the solution stirred and cooled till −70° C. on an actone bath with liquid nitrogen. 6.25 ml BuLi was added and the mixture stirred for 1 hour at −70° C. 10 ml of a 1M solution of anhydrous ZnCl$_2$ in THF were added and the solution mixed 2 hrs at −55° C., during which a dark red-brown tar formed, which was difficult to stir. 1.21 gr. (5 mmol) of Br-T-Br and about 25 mg of Pd(dppf)Cl$_2$ were added and the reaction mixture was allowed to reach room temperature slowly. The mixture was then stirred and refluxed overnight (20 hrs). An orange precipitate formed. The reaction mixture was cooled on an ice bath and mixed for one hour, whereafter the precipitate was collected on a Büichner filter. The precipitate was rinsed with chloroform and pentane and dried in vacuo. Yield: 2.163 gr. oranje powder. Elemental analysis: found% C 41.54, H 2.76, N 4.47, S 14.0, Cl 9.32, Br 8.33, Zn 13.5. Part of the precipitate was treated with a 1% EDTA (Titriplex III) solution (stirring at about 80° C. for 1 hour). The precipitate was filtered, washed with portions of ethanol and ether and dried in air, yielding a yellow/brown powder, partly soluble in chloroform. $^1$H-NMR (300 MHz, CDCl$_3$) yielded a spectrum corresponding to pure PT$_3$P. The same reaction and procedure of purification was followed for coupling PT-ZnCl to Br-T$_2$-Br, Br-T$_3$-Br and Br-T$_4$-Br. The coupling of Br-T$_2$-Br yielded 3.47 gr. of red powder. Elemental analysis: found% C 41.23, H 2.80, N 3.81, S 16.5, Cl 9.44, Br 9.72, Zn 11.4. EDTA treatment yielded an orange/brown powder. The fraction soluble in chloroform appeared to be largely PT$_3$-Br, as evidenced from the $^1$H-NMR spectrum. The coupling product with Br-T$_3$-Br yielded 3.60 gr. of dark red powder. Elemental analysis: found% C 42.32, H 2.95, N 3.09, S 19.7, Cl 7.46, Br 8.47, Zn 9.27. Also this substance was EDTA-treated, which gave a red/brown precipitate. $^1$H-NMR analysis, of the fraction that was soluble in chloroform, indicated the presence of PT$_4$-Br and PT$_5$P: $^1$H-NMR. (300 MHz, CDCl$_3$) of PT$_4$-Br: ∂=8.60 (d, broad), ∂=7.47 (d, 3.8 Hz), ∂=7.44 (d, J=3.9 Hz), ∂=7.20 (d, J=3.7 Hz), ∂=7.16 (d, Y=4.1 Hz), ∂=7.11 (d, J=3.5 Hz), ∂=7.09 (d, J=3.8 Hz), ∂=7.05 (d, J=3.6 Hz), ∂=6.99 (d, J=3.9 Hz), ∂=6.93 (d, J=3.9 Hz) and PT$_5$P: ∂=8.60 (d, broad), ∂=7.47 (d, 3.8 Hz), ∂=7.44 (d, J=3.9 Hz), ∂=7.20 (d, J=3.7 Hz), ∂=7.16 (d, J=4.1 Hz), ∂=7.11 (d, J=3.5 Hz), ∂=7.11 (s).

Methylations 50 or 100 mg of the pyridylthiophene derivative was dissolved in 50 ml of chloroform and 1 ml of methyliodide added. In case of PT$_3$P and PT$_4$P only very little (<10 mg) substance was used and about 10 ml of chloroform. After mixing, the methylation was allowed to proceed for one week at room temperature in a closed erlenmeyer flask, during which neat crystals of the product formed. The products were collected on a Büchner filter and washed with chloroform. It was noticed that under these conditions $PT_2P$ was monomethylated and $PT_3P$ and $PT_4P$ dimethylated.
Analytical data:

MeI-PT:

Elemental analysis: found% (theory%) C 38.84 (39.62), H 3.30 (3.32), N 4.82 (4.62), S 10.3 (10.6), I 40.3 (41.9); $^1$H-NMR (300 MHz, DMSO-$d_6$): $\partial$=8.86 (2H, d, J=6.9 Hz), $\partial$=8.34 (2H, d, J=6.9 Hz), $\partial$=8.23 (1H, dd, J=1.2 and 3.8 Hz), $\partial$=8.10 (1H, dd, J=1.0 and 5.0 Hz), $\partial$=7.38 (1H, dd, J=3.8 and 5.0 Hz), $\partial$=4.24 (3H, s)

MeI-PT-Br:

Elemental analysis: found% (theory%) C 31.21 (31.44), H 2.43 (2.37), N 3.94 (3.67), S 8.71 (8.39), Br 23.1 (20.9), I 33.3 (33.2); $^1$H-NMR (200 MHz, DMSO-$d_6$): $\partial$=8.89 (H, dd, J=6.9 Hz), $\partial$=8.31 (H, dd, J=6.5 Hz), $\partial$=8.08 (1H, d, J=3.7 Hz), $\partial$=7.56 (1H, d, J=4.1 Hz), $\partial$=4.24 (3H, s).

MeI-PT-I:

Elemental analysis: found% (theory%) C 27.38 (27.99), H 2.09 (2.11), N 3.39 (3.26), S 7.39 (7.47), 158.0 (59.2); $^1$H-NMR (200 MHz, DMSO-$d_6$): $\partial$=8.86 (2H, d, J=6.5 Hz), $\partial$=8.28 (2H, d, J=6.1 Hz), $\partial$=7.92 (1H, d, J=4.1 Hz), $\partial$=7.64 (1H, d, J=3.7 Hz), $\partial$=4.22 (3H, s).

MeI-$PT_2P$:

Elemental analysis: found% (theory%) C 44.37 (49.36), H 3.22 (3.27), N 5.47 (6.06), S 12.1 (13.9), I 26.1 (27.5); $^1$H-NMR (300 MHz, DMSO-$d_6$): $\partial$=8.86 (2H, d, 7.1 Hz), $\partial$=8.61 (2H, d, J=5.1 Hz), $\partial$=8.32 (2H, d, J=7.0 Hz), $\partial$=8.26 (1H, d, J=4.4 Hz), $\partial$=7.90 (1H, d, J=3.5 Hz), $\partial$=7.72 (1H, d, J=4.0 Hz), $\partial$=7.68 (3H, d, J=4.0 Hz), $\partial$=4.24 (3H, s).

MeI-$PT_3P$-MeI:

Elemental analysis: found% (theory%) C 38.27 (41.99), H 3.70 (2.94), N 3.75 (4.08), S 15.5 (14.0), I 34.8 (37.0); $^1$H-NMR (300 MHz, DMSO-$d_6$): $\partial$=8.87 (4H, d, J=7.0 Hz), $\partial$=8.33 (4H, d, J=7.1 Hz), $\partial$=8.27 (2H, d, J=4.1 Hz), $\partial$=7.73 (2H, d, J=4.1 Hz), $\partial$=4.22 (6H, s).

MeI-$PT_4P$-MeI:

$^1$H-NMR (300 MHz, DMSO-$d_6$): $\partial$=8.85 (4H, d, J=6.9 Hz), $\partial$=8.31 (4H, dd, broad), $\partial$=8.26 (2H, d, J=4.1 Hz), $\partial$=7.69 (2H, d, J=4.0 Hz), $\partial$=7.61 (2H, d, J=3.9 Hz), $\partial$=7.52 (2H, d, J=3.9 Hz), $\partial$=4.24 (6H, s).

I claim:

1. A conductor structure for conducting electrons, comprising a first end structured and arranged to receive electrons and a second end structured and arranged to donate electrons, wherein the conductor structure comprises, acting as a molecular conductor conducting electrons along its molecular structure, a compound with the following general formula (I):

wherein n represents an integer from 1 to 12 the groups X and Y are identical or different and denote functional substituents bound to the pyridine nitrogen, or one or both of X and Y are absent, and R, being identical or different, represent a hydrogen atom or an aliphatic side chain introduced for enhancing the solubility of the molecule in organic solvents, containing any number of carbon atoms.

2. A conductor structure according to claim 1, wherein n represents an integer from 2 to 12.

3. A conductor structure according to claim 1, wherein R, being identical or different, represent a hydrogen atom or a branched or unbranched alkyl or alkoxy group.

4. A conductor structure according to claim 1, wherein one or both of the groups X and Y is an aliphatic branched or unbranched alkyl side chain containing a number of carbon atoms between 1 and 20.

5. A conductor structure according to claim 1, wherein one or both of the groups X and Y contains an aliphatic alkyl chain containing a number of carbon atoms between 1 and 20, attached at its one end to the pyridine nitrogen and having at its other end a functional group, said group serving as a tether group used for attachment to an organic or inorganic surface.

6. A conductor structure according to claim 5, wherein one or both of the groups X and Y is selected from the group consisting of:

where x and y are integers in the range of 1 to 20.

7. A conductor structure according to claim 1, wherein one or both of the groups X and Y denotes a metal complex with formula —M—L, in which M is a metal ion forming a coordination bond to the pyridine nitrogen, and L is an external mono- or multidendate ligand or functional group bound to the metal ion by a coordination bond.

8. A conductor structure according to claim 7, wherein the metal ion is selected from a group consisting of copper, nickel, ruthenium and osmium.

9. A conductor structure according to claim 7, wherein the ligand L or the complex M-L is a redox protein or redox enzyme.

10. A conductor structure according to claim 1, wherein the group X or Y is a redox protein or redox enzyme.

11. An electronic device used for diagnostic determinations of a chemical species, containing a molecular preparation essential for generating an electronic response in the form of a change in current potential, conductivity or capacitance, said molecular preparation being an electron-conducting molecular preparation according to claim 10.

12. An electronic device used for diagnostic determinations of a chemical species, containing a molecular preparation essential for generating an electronic response in the form of a change in current, potential, conductivity or capacitance, said molecular preparation being an electron-conducting molecular preparation according to claim 1.

13. A membrane for passing electrons, containing electron-conducting parts in a substantially insulating membrane, wherein a molecular preparation is incorporated to form electronic conductors in the substantially insulating membrane, said molecular preparation having the following general formula (I):

wherein n represents an integer from 1 to 12 the groups X and Y are identical or different and denote functional substituents bound to the pyridine nitrogen, or one or both of X and Y are absent, and R, being identical or different, represent a hydrogen atom or an aliphatic side chain introduced for enhancing the solubility of the molecule in organic solvents and containing any number of carbon atoms.

14. A membrane according to claim 13, wherein in the molecular preparation n represents an integer from 2 to 12.

15. A membrane according to claim 13, wherein in the molecular preparation one or both of the groups X and Y is an aliphatic branched or unbranched alkyl side chain containing a number of carbon atoms between 1 and 20.

16. A membrane according to claim 13, wherein in the molecular preparation the group X or Y is a redox protein or redox enzyme.

17. An electronic device containing a membrane according to claim 16 attached to an electrode surface.

18. A membrane according to claim 13, wherein the membrane is selected from the group consisting of a molecular monolayer, a molecular bilayer, a molecular multilayer and a thin polymer layer.

19. An electronic device containing a membrane according to claim 13 attached to an electrode surface.

20. Compound of the general formula (I):

wherein n represents an integer from 3 to 12 the groups X and Y are identical or different and denote functional substituents bound to the pyridine nitrogen, or one or both of X and Y are absent, and R, being identical or different, represent a hydrogen atom or an aliphatic side chain introduced for enhancing the solubility of the molecule in organic solvents.

* * * * *